United States Patent [19]

Nagarajan et al.

[11] 3,976,778

[45] Aug. 24, 1976

[54] IMIDAZOLES AND PROCESSES FOR THEIR PRODUCTION

[75] Inventors: Kuppuswamy Nagarajan; Vishwa Prakash Arya; Thomas George, all of Bombay, India

[73] Assignee: Ciba-Geigy Corporation, Ardsley, N.Y.

[22] Filed: Sept. 23, 1974

[21] Appl. No.: 508,603

[30] Foreign Application Priority Data

Aug. 13, 1973 India...................................... 266/73
Sept. 24, 1973 Switzerland....................... 13667/73

[52] U.S. Cl. ............................ 424/273; 260/243 B; 260/247.1 M; 260/247.2 A; 260/250 BN; 260/293.7; 260/309; 260/309.7
[51] Int. Cl.² ............. A61K 31/415; C07D 233/92; C07D 233/54
[58] Field of Search................... 260/309.7; 424/273

[56] References Cited

UNITED STATES PATENTS

| | | | |
|---|---|---|---|
| 3,458,528 | 7/1969 | Gal | 260/309.7 X |
| 3,472,864 | 10/1969 | Henry et al. | 260/309.7 X |
| 3,719,759 | 3/1973 | Sarett et al. | 424/273 |
| 3,832,532 | 8/1974 | Ilvespää | 260/309.7 |

OTHER PUBLICATIONS

Protiva et al., vol. 52, Chem. Abstracts, 1147a.

*Primary Examiner*—Ethel G. Love
*Attorney, Agent, or Firm*—Joseph G. Kolodny; John J. Maitner; Theodore O. Groeger

[57] ABSTRACT

The present invention relates to processes for the preparation of new imidazoles, especially of 4- or 5-nitro-imidazoles, substituted by tetrahydroimidazoles which may be substituted and to such compounds which are valuable chemotherapeutica in the treatment of gram-negativ bacteria, protozoa and worms.

18 Claims, No Drawings

IMIDAZOLES AND PROCESSES FOR THEIR PRODUCTION

The present invention relates to imidazoles and processes for the production thereof. The invention provides new imidazoles of the formula I

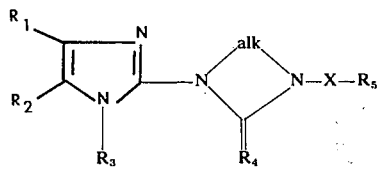

wherein one of the groups $R_1$ and $R_2$ is a hydrogen or lower alkyl and the other a nitro group, $R_3$ is a lower alkyl, hydroxyloweralkyl, loweralkoxyloweralkyl, lower alkylsulphonylloweralkyl or aminoloweralkyl, $R_4$ is an oxo or thioxo group, X is a carbonyl, thiocarbonyl, sulphinyl or sulphonyl group and $R_5$ when X is a carbonyl group is a lower alkoxy, amino, loweralkylamino or diloweralkylamino group, and when X is a thiocarbonyl, sulphinyl or sulphonyl, $R_5$ is a lower alkyl, aryl, amino, alkylamino or diloweralkylamino group and alk is a lower alkylene group and their salts.

The term "lower" as used hereinbefore or hereinbelow in connection with the definition of organic compounds, groups and radicals, signifies that such compounds, groups and radicals contain up to and including 7 carbon atoms preferably up to 4 carbon atoms.

Examples of lower alkyl groups are preferably methyl, ethyl, n-propyl, isopropyl, n-butyl, isobutyl, sec. butyl, tert. butyl, n-pentyl, isopentyl, neopentyl, n-hexyl, iso-hexyl or n-heptyl groups.

Hydroxyloweralkyl groups have at most 7 carbon atoms, particularly up to 4 carbon atoms, wherein the lower alkyl portion has the above mentioned meaning, like e.g. hydroxymethyl, 3-hydroxy-n-propyl and particularly 2-hydroxyethyl.

Loweralkoxyloweralkyl residues are e.g. those in which the lower part has up to 7 carbon atoms, particularly up to 4 carbon atoms e.g. methoxymethyl, ethoxymethyl, n-propoxymethyl, n-butoxymethyl, 2-(n-butoxy)-ethyl, 3-(n-propoxy)-propyl or in particular 2-methoxyethyl.

Loweralkylsulphonylloweralkyl residues are e.g. lower alkyl groups as mentioned above which carry a lower alkyl sulphonyl group such as methylsulphonylmethyl, ethylsulphonylmethyl, 2-methylsulphonylethyl, n-propylsulphonylmethyl, 2-n-propylsulphonylethyl, 3-n-propylsulphonyl-n-propyl or ethylsulphonylethyl and in particular 2-ethylsulphonylethyl.

Aminoloweralkyl is e.g. an above mentioned lower alkyl which carries an amino group, in particular a tertiary amino group. A tertiary amino group is e.g. diloweralkylamino, such as dimethylamino, N-methyl-N-ethylamino, diethylamino, di-n-propylamino or di-n-butylamino or loweralkyleneamino in which the lower alkylene part may be interrupted by a hetero atom such as oxaloweralkyleneamino, thialoweralkyleneamino or azaloweralkyleneamino, e.g. pyrrolidino, piperidino, morpholino, thiomorpholino, 2,6-dimethylthiomorpholino, piperazino, N'-methylpiperazino, or N'-(β-hydroxyethyl)-piperazino. Aminoloweralkyl is e.g. dimethylaminomethyl, diethylaminomethyl, 2-dimethylaminoethyl, pyrrolidinomethyl, 2-pyrrolidinoethyl, 3-pyrrolidino-n-propyl, piperidinomethyl, morpholinomethyl 2-morpholino-ethyl, 2-thiomorpholino-ethyl, piperazino-methyl, 2-piperazino-ethyl, N'-methylpiperazino-methyl, 3-(N-methylpiperazino)-n-propyl and N'-(β-hydroxyethyl)-piperazinomethyl.

The aryl group $R_5$ is an optionally substituted aryl residue e.g. a phenyl or naphthyl group optionally substituted by one or more than one substituent as well as an optionally substituted 5,6,7,8-tetrahydro-1-or 2-naphthyl residue. Preferred are optionally mono- or di-substituted phenyl or naphthyl radicals, particularly mono-substituted phenyl or naphthyl radicals and especially monosubstituted phenyl radicals.

The aryl residue $R_5$ may be substituted e.g. by the above-defined loweralkyl groups, loweralkoxy groups, halogen atoms such as chlorine, bromine or fluorine or by a trifluoromethyl group.

Lower alkoxy groups are e.g. the methoxy, ethoxy, n-propoxy, isopropoxy, n-butyloxy or n-pentyloxy groups, and loweralkylamino is e.g. methylamino, ethylamino and diloweralkylamino is e.g. dimethylamino, diethylamino or ethylmethylamino.

Lower alkylene is a branched or preferably a straight chain lower-alkylene e.g. with 2–4 carbon atoms in the alkylene residue, such as 1,2-propylene, 1,2,-butylene, 1,2-pentylene, 1,2-hexylene, 2-methyl-1,2-propylene, 2,3-butylene, 1,3-butylene, 1,3-propylene, 1,4-butylene or above all 1,2-ethylene.

The new compounds show valuable pharmacological properties. They show, in particular, activity against bacteria, especially against gram negative bacteria, protozoa e.g. trichomonads and amoeba and helminths, e.g. schistosomes and above all amoeba, as shown in experimental animals, e.g. on the liver of hamsters infected with Entamoeba histolytica, at a dose between 10 and 100 mg/kg p.o.. Thus, the new imidazoles are useful against amoeba, schistosomes, trichomonads and bacteria. Further, the new compounds are useful as starting materials or intermediates for the preparation of other compounds, in particular, therapeutically active compounds.

The invention refers particularly to compounds of formula Ia

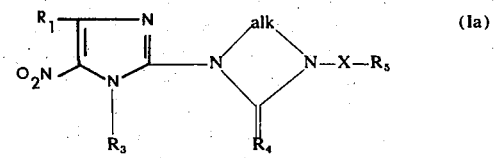

wherein $R_1$ represents hydrogen or a loweralkyl group, $R_3$ is loweralkyl, hydroxyloweralkyl, loweralkoxyloweralkyl, loweralkylsulphonylloweralkyl or aminoloweralkyl group, $R_4$ is an oxo group, X and $R_5$ have the earlier defined meanings and alk is a lower alkylene residue of 2–4 carbon atoms, their salts and N-oxides.

Furthermore the invention refers particularly to compounds of formula Ib,

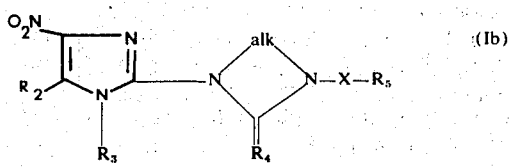

(Ib)

wherein $R_2$ represents hydrogen or a lower alkyl group, $R_3$ a lower alkyl, hydroxyloweralkyl, loweralkoxyloweralkly, loweralkylsulphonylloweralkyl or aminoloweralkyl group, $R_4$ is an oxo group, X and $R_5$ have the earlier defined meanings and alk is a lower alkylene residue of 2–4 carbon atoms, their salts and N-oxides.

Particularly the invention refers to compounds of formula Ia, wherein $R_1$, $R_3$, $R_4$ and alk have the meanings as defined under formula Ia, X is a carbonyl group and $R_5$ represents a loweralkoxy, amino, loweralkylamino or diloweralkylamino group and to compounds of formula Ib, wherein $R_2$, $R_3$, $R_4$ and alk have the meanings as defined under formula Ib, X is a carbonyl group and $R_5$ is a loweralkoxy, amino, loweralkylamino or diloweralkylamino group, their salts and N-oxides.

Also of particular interest are compounds of formulae Ia and Ib, wherein $R_1$ or $R_2$, $R_3$, $R_4$ and alk have the meanings defined above. X is a thiocarbonyl and $R_5$ a loweralkyl, loweralkoxy, aryl, amino, loweralkylamino or diloweralkylamino group, their salts and N-oxides.

Of particular interest are compounds of formulae Ia and Ib, wherein $R_1$ or $R_2$, $R_3$, $R_4$ and alk have the meanings defined above and X is a sulphinyl or sulphonyl group and $R_5$ is a lower alkyl, lower alkoxy, aryl, amino, loweralkylamino or diloweralkylamino group, their salts and N-oxides.

The invention concerns primarily of compounds of formulae Ia and Ib, wherein $R_1$ or $R_2$ have the meanings given under formula Ia or Ib, $R_3$ represents lower alkyl as for example methyl, ethyl or hydroxyloweralkyl as for example β-hydroxymethyl or β-hydroxypropyl, alk is 1,2-ethylene, X is a carbonyl group, $R_4$ is an oxo group and $R_5$ lower alkoxy, as for example methoxy, ethoxy, amino, loweralkylamino or diloweralkylamino, their salts and N-oxides.

Of similar interest are compounds of formulae Ia and Ib, wherein X is a thiocarbonyl, sulphinyl or sulphonyl group, $R_1$ or $R_2$ have the meaning given under formulae Ia or Ib, $R_3$ is a lower alkyl group as for example a methyl or ethyl group or lowerhydroxy alkyl, as for example, β-hydroxyethyl or β-hydroxypropyl and alk is 1,2-ethylene, $R_4$ represents an oxo group, and $R_5$ a loweralkoxy group, as for example a methoxy, or ethoxy group or an amino, loweralkylamino or diloweralkylamino group, their salts and N-oxides.

Among the nitroimidazole compounds which are to be mentioned especially are 1-(methylsulphonyl)-2-oxo-3-[1-methyl-5-nitro-imidazolyl (2)]-tetrahydroimidazole, 1-N,N-diethylcarbamoyl-2-oxo-3-[1-methyl-5-nitro-imidazolyl(2)]-tetrahydroimidazol and 1N,N-dimethylcarbamoyl-2-oxo-3-[1-methyl-5-nitro-imidazolyl-2)]-tetrahydroimidazol, 1N-ethylthiocarbamoyl-2-oxo-3-[1-methyl-5-nitro-imidazolyl-2]-tetrahydroimidazole, 1-N-methylthiocarbamoyl-2-oxo-3-[1-methyl-5-nitroimidazolyl-2]-tetrahydroimidazole whose use result in eradication of abscess on the liver of healthy hamsters infected with Entamoeba histolytica.

These compounds are thus useful as antiamoebic preparations for which purposes doses of 10 to 100 mg/kg p.o. are indicated.

The new imidazoles are prepared by methods which are in themselves known. For example, compound of the formula I may be prepared by the reaction of a compound of the formula II

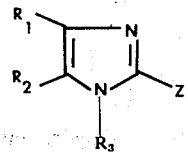

(II)

wherein $R_1$, $R_2$ and $R_3$ have the meanings defined earlier and Z is a reactive esterified hydroxy group, a free or etherified mercapto group, an ammonium group, a sulphinyl group or a sulphonyl group with a compound of the formula III

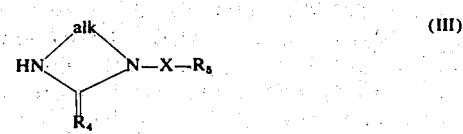

(III)

wherein $R_4$, $R_5$, alk and X have the meanings defined under formula I.

A reactive esterified hydroxy group Z is, in particular, a hydroxy group that is esterified with an inorganic or organic acid, above all hydrohalic acid, such as hydrochloric, hydrobromic or hydroiodic acid, sulphuric acid or an organic sulphonic acid, such as an aromatic sulphonic acid, e.g. benzenesulphonic, p-bromobenzene sulphonic or p-toluenesulphonic acid, or an aliphatic sulphonic acid, such as an alkanesulphonic acid e.g. methanesulphonic acid or ethanesulphonic acid.

A reactive etherified hydroxy group is e.g. a hydroxy group etherified with an aromatic, aliphatic or above all a lower aliphatic alcohol, such as an optionally substituted phenoxy group or an alkoxy group, above all a lower alkoxy, especially a methoxy or ethoxy group.

An etherified mercapto group is e.g. an optionally substituted phenylmercapto or benzyl mercapto group or in particular a lower alkyl mercapto group, such as ethyl or methylmercapto group.

An ammonium group is, in particular, a quarternary ammonium group, above all a tri-loweralkyl ammonium group e.g. trimethyl or triethylammonium group or the cation of an aromatic nitrogen base e.g. pyridinium or quinolinium group.

A sulphonyl group is, in particular, that of an organic sulphonic acid, especially an aromatic sulphonic acid residue. The group Z stands preferably for benzenesulphonyl, p-bromobenzenesulphonyl, p-toluenesulphonyl or above all methyl sulphonyl.

The reaction is carried out in the presence of a basic condensing agent or the compound of formula II is reacted in the form of its N-metal derivatives, such as N-alkali metal derivatives e.g. by the treatment of the compound of formula III with an amide, hydride, an hydroxide or alcoholate of an alkali metal such as lithium, sodium or potassium without isolation of the intermediate, if necessary. Selected basic condensing agents are e.g. alkali earth hydroxide, such as sodium hydroxide, potassium hydroxide and calcium hydroxide or organic tertiary bases, such as trialkylamine, e.g. trimethylamine and triethylamine or pyridine. The reaction is carried out, if necessary, at a higher temperature and/or in the presence of an inert solvent, such as those with polar functional groups e.g. dimethylformamide, dimethylacetamide, dimethyl-sulphoxide, acetonitrile or a cyclic-aliphatic-ether such as dioxan or tetrahydrofuran.

According to a second process compounds of formula I are prepared by nitration of a compound of the formula IV

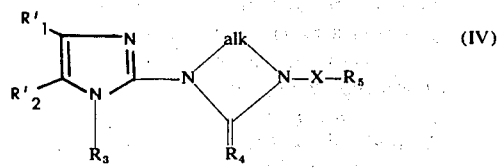

wherein one of the residues $R'_1$ and $R'_2$ is a hydrogen atom and the other a hydrogen or a loweralkyl group.

The nitration of a compound of the formula IV is carried out by the usual nitration methods e.g. with nitric acid or a nitrating mixture or a mixture of nitric acid and a carboxylic acid, such as acetic acid, wiith a mixed anhydride of nitric acid and a carboxylic acid such as acetic acid, by thermal and/or acid treatment of a nitrate salt of the compound IV, with dinitrogen tetroxide, e.g. dinitrogen tetroxide/BF$_3$, if necessary, in a suitable solvent e.g. nitrohydrocarbon, such as nitroalkane e.g. nitromethane or with nitrogen tetroxide e.g. in acetonitrile, or with a N-nitroderivative.

N-nitro compounds are e.g. nitroamides, such as nitrourethanes, nitroguanidine, nitrobiuret and nitro urea e.g. ethylene dinitrourea.

The acid treatment of a nitrate salt of a compound of the formula IV may be carried out at a higher temperature between 40°–100°, e.g. between 60°–80°.

Compounds of formula I may be prepared according to a third process which comprises reacting a compound of formula V

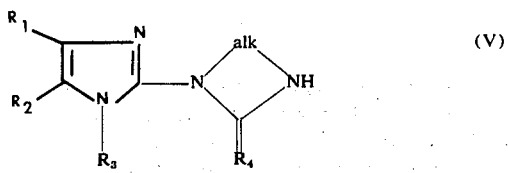

wherein $R_1$, $R_2$, $R_3$, $R_4$ and alk have the meanings given before with a compound Z—X—R$_5$ (VI) wherein X and R$_5$ have the previously defined meanings and Z is a reactive esterified hydroxy group, a reactive etherified hydroxy group, a free or etherified mercapto group, an ammonium group, a sulphinyl group, a sulphonyl group or a free or functionally converted carboxyl, thiocarboxyl group or dithiocarboxyl group.

The reactive esterified hydroxyl group and other reactive groups defined for the group Y are the same as those described earlier for the group Z under the first process. The reaction is carried out under conditions used for such condensations and described earlier.

According to a fourth process nitroimidazoles of formula I are prepared by reacting a compound of formula VII

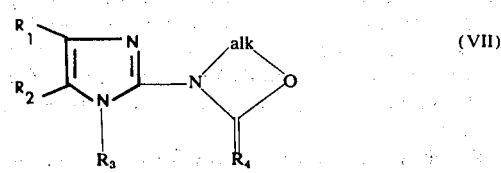

wherein $R_1$, $R_2$, $R_4$ and alk have earlier defined meanings, with a compound of the formula R$_5$—X—NH$_2$ (VIII), wherein R$_5$ and X have the meanings defined earlier.

The reaction of a compound of the formula VII with a compound of the formula R$_5$—X—NH$_2$ (VIII) is preferably carried out with the application of heat, if necessary, in a high boiling inert solvent. It may also be carried out with the aid of suitable dehydrating agents such as phosphorous pentoxide.

Compounds of the general formula I may be converted into one another by know methods. For example, compounds wherein $R_3$ is a hydroxyloweralkyl may be converted to loweralkoxy-loweralkyl by alkylation with suitable alkylating agents.

For example, hydroxyloweralkyl substituted derivatives may be reacted with a reactive ester such as an ester of a lower alkanol, preferably in the presence of a basic condensation agent, as for example in the presence of an alkali metal hydroxide or with a diazoloweralkane, such as diazomethane, preferably in the presence of boron trifluoride. However, it is also possible to convert a hydroxy-lower alkyl radical $R_3$ into an amino-lower alkyl radical in the usual manner. Thus it is possible first to convert a resulting hydroxy-lower alkyl compound into a compound possessing a reactive esterified hydroxy-lower alkyl radical, a reactive ester being, in particular, an ester of strong inorganic or organic acids, such as, in particular, hydrogen halide acids, for example hydrochloric acid, hydrobromic acid or hydroiodic acid, toluenesulphonic acids, such as, in particular, arylsulphonic acids, for example benzenesulphonic acid or toluenesulphonic acids, alkylsulphonic acids or sulphuric acid. For example, a hydroxy-lower alkyl compound can be converted into a halogeno-lower alkyl compound by treatment with halogenating agents, such as thionyl chloride, phosphorous oxychloride or phosphorous pentabromide. In the resulting reactive ester the reactive esterified hydroxyl group can then be replaced in the usual manner by an amino group, for example by treatment with corresponding amines.

In compounds of the formula I when $R_3$ is an amino-lower alkyl group containing at least one replaceable hydrogen atom attached to the nitrogen, this can be substituted. For example, in compounds of the formula I in which $R_3$ is a primary or secondary amino group, such groups may be substituted by reaction with a reactive ester of an alcohol corresponding to the substituent of the amino group of the aminoloweralkyl radical.

Furthermore it is possible to N-oxidise an imidazole of the formula I which carries a N-heterocyclic radical.

The oxidation is carried out in the usual manner, for example with N-oxidising agents, such as hydrogen peroxide, ozone, inorganic per-acids, for example persulphuric acids, such as Caro's acid, or especially organic peroxy compounds, above all organic per-acids, such as peracetic acid, pertrifluoroacetic acid, perbenzoic acid or monoperphthalic acid, which can also be substituted, for example by halogen atoms, such as chlorine atoms, for instance chloromonoperphthalic acid or m-chloroperbenzoic acid or tertiary hyperoxide compounds, such as tert.-butyl peroxide or cumene peroxide, optionally in the presence of catalysts such as vanadium, titanium or molybdenum compounds.

Resulting compounds of the formula I, with a N-oxidised N-heterocyclic radical, can be converted by reduction into the corresponding compounds of the formula I, with a N-heterocyclic radical.

The reduction is carried out in the usual manner, advantageously by the action of phosphorous halides.

Resulting compounds of the formula I, in which X is a sulphinyl group can be oxidised to the S-dioxides (sulphones).

The oxidation to the sulphones can be carried out in a manner which is in itself known, for example by reaction with a S-oxidising agent, such as hydrogen peroxide, per-acids, especially peracetic acid, perbenzoic acids or monoperphthalic acids, which can also be substituted, for example by halogen atoms, 1-chlorobenzotriazole, chromic acid, potassium permanganate, hypohalites or nitric acid, nitrous gases and the like, or electrolytically. In these reactions, whilst on warming and/or using at least 2 mol equivalents of the oxidising agent the sulphones are obtained.

Resulting S-dioxides can be reduced to the corresponding S-oxides of the formula I, for example with a reducing agent, such as a di-light metal hydride, for example with sodium boronhydride, or a light metal hydride such as diborane or a boronhydride-etherate, for example $BH_3$-tetrahydrofurane, or above all dichloroborane or, for example, with acetylic chloride, sulphites or hydriodic acid, or especially with triphenylphosphine.

In the above reductions care must be taken, where relevant, that further groups which can be reduced are not attacked. Thus care must in particular be taken, during the reduction, that any halogen atoms bound to aromatic rings which may be present are not replaced by hydrogen.

Very particularly, it is necessary to ensure that the nitro group ($R_1$ or $R_2$) is not reduced. Catalysts which are not affected by sulphur are preferentially to be used, and if necessary the hydrogen absorption should be followed volumetrically and the hydrogenation stopped after the calculated amount has been absorbed.

Compounds of the formula I which contain a nitro group as the radical $R_2$ can be rearranged to give the corresponding 4-nitroimidazoles, that is to say compounds of the formula I which contain a nitro group as the radical $R_1$. Such a rearrangement is effected, for example, by the action of, for instance, an excess of alkali metal iodide, especially potassium iodide, in the presence of an inert solvent, preferably a solvent with polar functional groups, such as dimethylformamide, dimethylacetamide, dimethylsulphoxide, acetonitrile or hexamethylphosporic acid triamide.

The rearrangement of $R_2$=nitro compounds into $R_1$=nitro compounds of the formula I can also be effected by the action of an iodide which corresponds to the radical $R_3$, namely $R_3I$, such as for example, the action of methyl iodide on compounds of the formula I which contain a methyl group as the $R_3$ radical. In this rearrangement, the unsubstituted nitrogen atom of the imidazole ring is quaternised. Thereafter, the quaternary salt is pyrolised. This rearrangement also takes place, for example, in the presence of an inert solvent, preferably the solvents described above.

The subsequent conversion can be carried out individually or in combination and in optional sequence. Care must be taken in individual operations that other functional groups are not attacked.

The reactions of this invention are carried out in the usual manner, at room temperature or with cooling or heating, under atmospheric or superatmospheric pressure, if necessary, in the presence of diluents, catalysts and condensing agents, and/or in the atmosphere of an inert gas, e.g. nitrogen.

Compounds of the formula III according to the first process are prepared by the action of a compound of the formula IX

where alk and $R_4$ have the meanings given before, e.g. an imidazolidin-2-one or a hexahydro-pyrimidin-2-one with a compound of the formula $R_5$—X—Z, wherein $R_5$, X and Z have the earlier defined meanings.

The compounds of the formula IV according to the second process are prepared by the reaction of a suitable imidazole derivative carrying a replaceable group of the type Z of formula II with a compound of the formula III according to the methods described under the first process for such condensation.

Compounds of the formula VII according to the fourth process are prepared by the reaction of an imidazole derivative carrying a replaceable group in the 2-position with a compound of the formula X

wherein alk and $R_4$ have the meanings defined earlier, compounds of the formula X are, for example, oxazolid-2-ones or 1,3-oxazine-2-ones.

The new nitro-imidazoles described herein as intermediates and starting materials also show valuable pharmacological properties. Thus, they show, in particular, at a dosage of 10 to 100 mg/kg p.o. action against bacteria especially gram negative bacteria, protozoa and worms, for example, trichomonads, schistosomes, coccidia and, particularly, amoeba as can be shown in animal experiments, for example, from the liver of healthy hamsters artificially infected with Entamoeba histolytica. Imidazoles of this invention can, therefore, in particular, be used as agents against amoeba, schistosomes, trichomonads and bacteria.

Depending on the process conditions and the starting substances, the final substances are obtained in the free form or in the form of their acid addition salts which is also included in the invention. Thus, for example, basic, neutral or mixed salts and where relevant also hemihydrates, monohydrates, sesquihydrates or polyhydrates thereof can be obtained. The acid addition salts of the new compounds can be converted into the free compound in a manner which is in itself known, for example with basic agents, such as alkalis or ion exchangers. on the other hand, the resulting free bases can form salts with organic or inorganic acids. The acids used for the manufacture of acid addition salts are in particular those suitable for forming therapeutically usable salts. As examples of such acids there may be mentioned: hydrogen halide acids, sulphuric acids, phosphoric acids, nitric acid, perchloric acid, aliphatic, alicyclic, aromatic or heterocyclic carboxylic acids or sulphonic acids, such as formic acid, acetic acid, propionic acid, succinic acid, glycolic acid, lactic acid, malic acid, tartaric acid, citric acid, ascorbic acid, maleic acid, hydroxymaleic acid or pyruvic acid; phenylacetic acid, benzoic acid, or p-aminobenzoic acid, anthranilic acid, p-hydroxybenzoic acid, salicylic acid or p-aminosalicylic acid, embonic acid, methanesulphonic acid, ethanesulphonic acid, hydroxyethansulphonic acid and ethylenesulphonic acid; halogenobenzenesulphonic acid, toluenesulphonic acid, naphthalenesulphonic acid or sulphanilic acid; methionine, tryptophane, lysine or arginine.

These or other salts of the new compounds such as, for example, the picrates, can also serve for the purification of the resulting free bases, by converting the free bases into salts, isolating these and again liberating the bases from the salts. Because of the close relationships between the new compounds in the free form and in the form of their salts, the free compounds are where appropriate also to be understood to include the corresponding salts, in the preceding and following text.

The invention also relates to those embodiments of the process in which a process is stopped at any stage or in which a compound obtainable as an intermediate product at any stage is used as the starting compound and the missing steps are carried out, or a starting substance is formed under the reaction conditions or used, where relevant, in the form of a salt and/or racemate or optical antipode.

Depending on the number of the asymmetrical C atoms and on the choice of the starting substances and procedures, the new compounds can be in the form of racemate mixtures, racemates or optical antipodes.

Racemate mixtures can be separated into the pure racemates on the basis of the physico-chemical differences of the constituents, in a known manner, for example by chromatography and/or fractional crystallisation.

Pure racemates can be resolved into the diastereomers according to known methods, for example by recrystallisation from an optically active solvent, with the aid of microorganisms or by reaction with an optically active acid which forms salts with the racemic compound and separation of the salts obtained in this manner, for example on the basis of their different solubilities, and from the diastereomers the antipodes can be liberated by the action of suitable agents. Particularly customary optically active acids are, for example, the D- and L- forms of tartaric acid, di-o-toluyl-tartaric acid, malic acid, mandelic acid, camphor-10-sulphonic or quinine acid. Resulting salts may be converted into other salts or into the free and optically active bases, and an optically active base may be converted into an acid addition salt by the methods referred to above.

According to their antimicrobial activity the compounds of formula I, their 5-N-oxides and their salts may be used to protect a high molecular weight hydrophobic or other organic material susceptible to bacterial or other microbial deterioration by contacting the organic material with, impregnating in or otherwise treating with, the compounds in amounts up to about 5 % by weight. The compounds also find application as growth-promoting additives to animal feedstuffs, to which they may be added in proportion of from 5 to 500 parts per million.

Accordingly, the invention also provides a therapeutic composition comprising an antimicrobially effective proportion of a compound of formula I, or their 5-N-oxides or pharmaceutically acceptable salts thereof and a pharmacologically acceptable solid carrier or liquid diluent.

The pharmaceutical compositions according to the invention contain at least one compound of the general formula I, or their 5-N-oxides or a pharmaceutically acceptable salt thereof as active substance together with a conventional pharmaceutical carrier. The type of carrier actually used depends to a great extent on the intended application; for external use, for example in disinfecting healthy skin, disinfecting wounds and in treating dermatoses and affections of the mucous membranes caused by bacterial or fungi, ointments, powders and tinctures are used in particular. The ointment bases may be anhydrous, for instance they can consist of mixtures of wool fat and soft paraffin, or they can consist of aqueous emulsions in which the active substance is suspended. Suitable carriers for powders are, for instance, rice starch and other starches; the bulk weight of the carriers may be made lighter, if desired, for example by adding highly despersed silicic acid, or may be made heavier by adding talcum. The tinctures may contain at least one active ingredient of the formula I, or 5-N-oxides thereof or a salt thereof in aqueous ethanol, in particular 45 % to 75 % ethanol, to which 10 % to 20 % of glycerol may be added, if desired. Solutions prepared from polyethylene glycol and other conventional solubility promoters, and also, optionally from emulsifying agents, may be used with particular advantage in disinfecting healthy skin. The content of active ingredient in pharmaceutical compositions for external application is preferably in the range of from 0,1 % to 5 %.

Gargles or concentrates for their preparation, and tablets for slow dissolution in the mouth, are suitable for the disinfection of the mouth and throat. The former are preferably prepared from alcoholic solutions containing 1 % to 5 % of active substance to which glycerol or flavourings may be added. Lozenges that is solid dosage units, preferably have a relatively high content of sugar or similar substances and a relatively low content of active substance, for instance 0,2 to 20 % by weight, as well as the usual convential additives such as binding agents and flavourings.

Solid dosage units, in particular tablets, dragees (sugar coated tablets) and capsules, are convenient for use in intestinal disinfection. These units preferably contain from 10 % to 90 % of the compound of the general formula I, their 5-N oxides or a salt thereof to enable the administration of daily doses of from 0,1 to 2,5 grams to adults, or of suitably reduced doses to children to be made. Tablets and dragee cores are produced by combining the compounds of the general formula I, their 5-N oxides or a pharmaceutically acceptable salt thereof with solid, pulverulent carriers such as lactose, saccharose, sorbitol, maize starch, potato starch or amylopectin, cellulose derivatives or gelatines, preferably with the addition of lubricants such as magnesium or calcium stearate or polyethylene glycols of suitable molecular weight. Dragee cores may then be coated, for example with concentrated sugar solutions which can also contain gum arabic, talcum and/or titanium dioxide, or they may be coated with a lacquer dissolved in volatile organic solvents or mixtures of solvents. Dyestuffs can be added to these coatings, for instance to differentiate between varying dosages. Soft gelatine capsules and other closed capsules consist, for example, of a mixture of gelatines and glycerol and may contain, for example, mixtures of the compound of formula I, their 5-N oxides or a pharmaceutically acceptable salt thereof with polyethylene glycol. Hard gelatine capsules containing, for example, granulates of an active substance with solid pulverulent carriers, for instance lactose, saccharose, sorbitol, mannitol, starches (such as potato starch, maize starch or amylopectin), cellulose derivatives of gelatines, and magnesium stearate or stearic acid.

In all forms of administration compounds of the general formula I, their 5-N oxides or a salt thereof can be present as sole active ingredients or they can also be combined with other known pharmacologically active, and especially antibacterial and/or antimycotically or other antimicrobially active substances, for example to broaden the range of application. They can be combined for example, with 5,7-dichloro-2-methyl-8-quinolinol or other derivatives of 8-quinolinol or other derivatives of 8-quinolinol, with sulfamerazine or sulfafurazole or other derivatives of sulfanilamide, with chloramphenicol or tetracycline or other antibiotics, with 3,4',5-tribromosalicylanilide or other halogenated salicylanilides, with halogenated carbanilides, with halogenated benzoxazoles or benzoxazolones, with polychloro-hydroxy-diphenylmethanes, with halogen-dihydroxy-diphenyl sulphides, with 4,4'-dichloro-2-hydroxy-diphenylether or 2,4,4'-trichloro-2-hydroxydiphenylether or other polyhalogenhydroxydiphenylethers, or with bactericidal quaternary compounds or with certain dithiocarbamic acid derivatives such as tetramethylthiuram disulphide or with other nitrofurans. Also, carriers which themselves have favourable pharmacological properties may be used, for instance sulphur as a powder base or zinc stearate as a component of ointment bases.

The invention also provides a method of protecting an organic material susceptible to bacterial or other microbial attack which comprises treating the material with a compound of formula I, their 5-N oxides or an acid addition salt thereof. The organic material may be a natural or synthetic polymeric material, a proteinaceous or carbohydrate substance, or a natural or synthetic fibre or textile material formed therefrom.

The invention also provides an animal feedstuff composition comprising a compound of formula I, their 5-N oxides or a salt thereof in an amount sufficient to promote the growth of the animal fed with the composition.

Preparation of Tablets 100 g of 1-(methylsulphonyl)-2-oxo-3-[1-methyl-5-nitro-imidazolyl-(2)]-tetrahydroimidazole are mixed with 60.0 g of maize starch and 35.0 g of lactose, the mixture is moistened with a solution of 5.0 g of gelatin and 3.0 g of glycerol in 70.0 g of water and granulated through a sieve. The granulate is mixed with a mixture of 15.0 g of talcum, 10.0 g of maize starch and 2.0 g of magnesium stearate. The resulting mixture is pressed into 1,000 tablets, each containing 100 mg of active substance. If desired, the tablets can be grooved for better adaption of the dosage.

| Preparation of Dragées Composition | | for 1,000 dragées |
|---|---|---|
| I | 1-(methylsulphonyl)-2-oxo-3-[1-methyl-5-nitro-imidazolyl-(2)]-tetrahydroimidazole | 100.0 g |
| | Maize starch | 27.0 g |
| | Gelatine | 8.0 g |
| II | Glycerol | 2.0 g |
| | Distilled water q.s. ad 100 ml | |
| | Maize starch | 10.0 g |
| III | Talcum | 7.0 g |
| | Magnesium stearate | 1.0 g |
| | | 155.0 g |
| IV | White dragée coating | |
| | Shellac | 2.0 g |
| | Sugar | 50.0 g |
| | Talcum | 38.0 g |
| | Gum arabic | 7.4 g |
| | Colloidal silicon dioxide | 2.2 g |
| | Titanium dioxide | 0.4 g |

Composition I is granulated in the heat with composition II through a sieve of 1.2 mm mesh diameter. The dried granulate is mixed with composition III and the resulting mixture is pressed into 1,000 dragée cores. These are then coated with composition IV and dried. The dragées obtained weigh 255.0 mg and contain 100 mg of active substance.

| Preparation of Syrup Composition | for 1 liter |
|---|---|
| 1-(methylsulphonyl)-2-oxo-3-[1-methyl-5-nitro-imidazolyl-(2)]-tetrahydroimidazole | 100.0 g |
| Colloidal solicone dioxide | 13.0 g |
| p-Hydroxybenzoic acid methyl ester | 1.4 g |
| p-Hydroxybenzoic acid propyl ester | 0.6 g |
| | 115.0 g |
| | 115.0 g |
| Citric acid | 1.0 g |
| Sodium cyclamate | 5.0 g |
| Distilled water | 610.0 g |
| Glycerol | 100.0 g |
| Sodium carboxymethyl cellulose | 4.0 g |
| Sugar | 320.0 g |
| | 1155.0 g |

The active substance and the colloidal silicon dioxide are passed through a sieve of 1.2 mm mesh diameter (I).

The p-hydroxybenzoic acid esters, the citric acid and the sodium cyclamate are dissolved in the given amount of boiling distilled water, the glycerol is then added to this solution (II). The sodium carboxymethyl cellulose and the sugar are thoroughly mixed (III).

Composition III is then added at 75°C to Solution II under stirring until complete dissolution of III. The viscous, slightly turbid liquid is cooled to room temperature, filtered, if necessary, and mixed with composition I. Water is added to the resulting mixture up to the prescribed weight of 1,550.0 g and the syrup obtained is homogenized.

Some examples will now begin, all parts and percentages being by weight unless otherwise stated. The temperatures are given in centigrade.

EXAMPLE 1

To a solution of 7.95g 1-(methylthiocarbamoyl)-2-oxo-2,3,4,5-tetrahydroimidazole in 100 ml dimethyl formamide is added 2.4 g of a 50% slurry of sodium hydride in mineral oil. The mixture is heated and stirred at 50° for 30 min. 10.25g of 1-methyl-2-methanesulphonyl-5-nitroimidazole are now added and the mixture stirred at 100° for 4 hrs. The solution is concentrated in vacuo to a small volume and treated with water. The crystalline precipitate is filtered off, washed with water and ether. It is then recrystallized from alcohol to give 1-(methylthiocarbamoyl)-2-oxo-3-[1-methyl-5-nitroimidazolyl-(2)]-tetrahydroimidazole of the formula

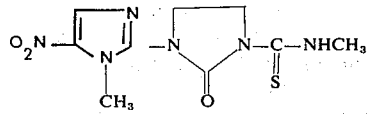

melting at 185°–187°.

The starting material 1-(methylthiocarbamoyl)-2-oxo-2,3,4,5-tetrahydroimidazole required for the above reaction is made as follows: a mixture of 86g ethyleneurea and 73g methylisothiocyanate is heated at 100° with stirring for 4 hrs. The crystalline mass obtained on cooling is rubbed with ether and water, filtered and washed with alcohol-ether mixture. It is recrystallized from methanol; m.p. 168°–171°.

EXAMPLE 2

To a solution of 4.7g 1-(benzylthiocarbamoyl)-2-oxo-2,3,4,5-tetrahydroimidazole in 50 ml dimethyl formamide is added 0.95g of a 50% of sodium hydride in mineral oil. The mixture is heated and stirred at 50° for 30 min. 4.1g of 1-methyl-2-methanesulphonyl-5-nitroimidazole are now added and the mixture stirred at 100° for 4 hrs. The solution is concentrated in vacuo to a small volume, treated with water and the mixture extracted with chloroform. The chloroform solution is washed with water, dried over sodium sulphate and evaporated in vacuo. Trituration of the residue with ether and crystallization of the resultant solid from chloroform-alcohol affords 1-(benzylthiocarbamoyl)-2-oxo-3-[1-methyl-5-nitroimidazolyl-(2)-]-tetrahydroimidazole melting at 178°–180°.

The starting thiocarbamoylimidazole required for the above reaction is made as follows: 86g ethyleneurea and 149g benzylisothiocyanate are treated together with stirring for 6 hrs. at 150°. Upon cooling, a solid mass is obtained, which is triturated with ether and then with hot alcohol and filtered. Recrystallization from chloroform-methanol gives 1-(benzylthiocarbamoyl)-2-oxo-tetrahydroimidazole.

EXAMPLE 3

To a solution of 5g of 1-(methylcarbamoyl)-2-oxo-2,3,4,5-tetrahydroimidazole in 50 ml dimethyl formamide is added 1.7 g of 50% slurry of sodium hydride in mineral oil. The mixture is stirred at 50° for 1 hr. A solution of 7.2g of 1-methyl-2-methanesulphonyl-5-nitroimidazole in 30 ml dimethyl formamide is now added and the mixture stirred at 100° for 3 hrs. The solvent is then removed in vacuo and water is added to the residue. The resultant red solution is then extracted with chloroform to give an oil, which upon rubbing with methanol affords a solid, recrystallized thrice from methanol to give 1-(methylcarbamoyl)-2-oxo-3-[1-methyl-5-nitroimidazolyl-(2)]-tetrahydromidazole melting at 176°–177°.

The starting methylcarbamoylimidazole for the above experiment is made by heating a mixture of 8.6 g ethyleneurea and 5.7 g methylisocyanate in a sealed tube at 130° for 3 hrs. and crystallizing the solid so obtained first from water and then from chloroform-methanol; m.p. 198°–200°.

EXAMPLE 4

To a solution of 16.4g 1-(methylsulphonyl)-2-oxo-2,3,4,5-tetrahydroimidazole in 120 ml dimethyl formamide is added 4.8 g of a 50% slurry of sodium hydride in mineral oil. The mixture is stirred at 50° for 30 min. A solution of 205g 1-methyl-2-methanesulphonyl-5-nitroimidazole in 70 ml dimethylformamide is now added and the mixture heated at 100° for 1 hr. The solvent is then removed in vacuo and the residue dissolved in water. Upon cooling, a crystalline precipitate is obtained, which is filtered off and recrystallized from acetone-methanol to afford 1-(methylsulphonyl)-2-oxo-3-[1-methyl-5-nitroimidazolyl-(2)]tetrahydroimidazole melting at 202°–204°.

The starting 1-(methylsulphonyl)-2-oxo-2,3,4,5-tetrahydroimidazole for the above reaction is made as follows: A mixture of 86 g ethyleneurea and 115 g methanesulphonyl chloride is heated for 6 hrs. at 120° with stirring, while a stream of nitrogen is bubbled in to remove hydrogen chloride. After cooling, water is added and the mixture heated on a steam bath till a crystalline powder is formed. This is filtered off, washed with alcohol-ether and recrystallized from methanol; m.p. 192°–195°.

EXAMPLE 5

To 8 g 1-(benzylthiocarbamoyl)-2-oxo-3-[1-methyl-5-nitroimidazolyl-(2)]-2,3,4,5-tetrahydroimidazole in 80 ml dimethylsulphoxide is added 5 ml of concentrated sulphuric acid and the solution is heated on a steam bath for 2 days. It is then diluted with water and the resultant precipitate filtered off. This is dissolved in ethyl acetate and ether added to give a solid. Crystallization from ethylacetateether affords 1-(benzylcarbamoyl)-2-oxo-3-[1-methyl-5-nitroimidazolyl-(2)]-2,3,4,5-tetrahydroimidazole melting at 113°–115°.

EXAMPLE 6

To a suspension of 1.5g 50% sodium hydride in 10 ml dry dimethyl formamide is added with stirring during 15 min. a solution of 5.8 g of 1-N-ethylthiocarbamoyl-2-oxo-tetrahydroimidazole in 20 ml dry dimethyl formamide. The reaction mixture is stirred under nitrogen at 50° for 30 min. and a solution of 4.5 g of 1-methyl-2-methylsulphonyl-5-nitroimidazole in 10 ml dry dimethyl formamide is added during 5 min., and then heated at 100° for 4 hrs. The solvent is evaporated off under vacuo; residue triturated with 50 ml water and extracted with ethylene dichloride. The ethylene dichloride extract is dried over anhydrous sodium sulphate and evaporated off to dryness. The residue is chromatographed over silica gel. The fraction that is eluted with 2% methanol in chloroform affords 1-N-ethylthiocarbamoyl-2-oxo-3-[1-methyl-5-nitroimidazolyl-(2)]-tetrahydroimidazole which melts at 213° after recrystallization from a mixture of methylenechloride and hexane.

The starting material required for the above reaction is prepared as follows: A mixture of 8.6 of ethyleneurea and 8.7 g of ethyl isothiocyanate is heated at 100° for 4 hrs. On cooling, the crystalline product was recrystallized from a mixture of ethanol and ether to afford 1-N-ethyl-thiocarbamoyl-2-oxo-tetrahydroimidazole which melts at 135°–136°.

EXAMPLE 7

To a suspension of 2.2 g 50% sodium hydride in 10 ml dry dimethyl formamide is added under stirring during 15 min., a solution of 8.7 g of 1-(N,N-dimethylsulphamoyl)-2-oxo-tetrahydroimidazole in 20 ml dry dimethyl formamide. The reaction mixture is stirred under nitrogen at 50° for 1 hr. and a solution of 9.25 g of 1-methyl-2-methylsulphonyl-5-nitroimidazole in 20 ml of dry dimethyl formamide is added all at once. The reaction mixture is heated under stirring and nitrogen at 95° for 3 hrs. The solvent is removed by distillation in vacuo and residue triturated with 45 ml water. The resulting suspension is extracted with ethylene dichloride, dried and evaporated to dryness. The residue is washed with hexane and triturated with acetone to give a crystalline solide. This is recrystallized from a mixture of methylene chloride and ether to afford 1-N,N(dimethyl-sulphamoyl)-2-oxo-3-[1-methyl-5-nitroimidazolyl-(2)]-tetrahydroimidazole which melts at 217°.

The starting material required for the above reaction is prepared as follows: A mixture of 17.2g of ethylene urea and 28.7 g of N,N-dimethyl sulphamoyl chloride is heated at 110° for 3 hours. The reaction mixture is cooled and triturated with 100 ml methanol. Some solid material separated which is discarded. The filtrate is evaporated off to dryness and the residue is dissolved in 5% methanol in chloroform and chromatographed on a column of 150 g of silica gel. The fraction which eluted with 2% methanol in chloroform is recrystallised from a mixture of methylenechloride and hexane to give 1-(N,N-dimethylsulphamoyl)-2-oxo-tetrahydroimidazole which melts at 129°.

EXAMPLE 8

A mixture of 34,4 g ethylene urea and 54,2 g N,N-diethylcarbamyl chloride is heated under nitrogen at 110° for 3 hrs. The reaction mixture is cooled and diluted with 200 ml acetone. It is filtered and the filtrate evaporated off to dryness. The oily product is chromatographed on a column of 450 g of silica gel. The fraction which eluted from 3% methanol in chloroform yields 1-(N,N-diethylcarbamoyl)-2-oxo-tetrahydroimidazole as a colourless oil.

To a suspension of 5.8 g 50% sodium hydrid in 20 ml dry dimethyl formamide is added under stirring during 15 min, a solution of 22 g of above mentioned 1-(N,N-diethylcarbamoyl)-2-oxo-tetrahydroimidazole in 40 ml of dry dimethyl formamide. The reaction mixture is stirred under nitrogen at 50° for 1 hr and a solution of 24.6 g of 1-methyl-2-methylsulphonyl-5-nitroimidazole in 40 ml of dry dimethyl formamide is added all at once.

The reaction mixture is worked up in the manner described under example 6 and the dark oily residue (36 g) is chromatographed over a column of 360 g of silica gel. The fraction that eluted with 2.5% methanol in chloroform yields a crystalline substance which is recrystallized from a mixture of methylene chlorid and hexane to give 1-N,N-diethylcarbamoyl-2-oxo-3-[1-methyl-5-nitro-imidazolyl-(2)]-tetrahydroimidazole which melts at 133°.

EXAMPLE 9

To a suspension of 24.5 g of 50% sodium hydride in 100 ml dry dimethyl formamide is added under stirring during 15 min, a solution of 78.5 g of 1-(N,N-dimethylcarbamoyl)-2-oxo-tetrahydroimidazole in 150 ml of dry dimethyl formamide. The reaction mixture is stirred under nitrogen at 50° for 1hr. and a solution of 102.5 g of 1-methyl-2-methyl-sulphonyl-5-nitroimidazole in 100 ml dry dimethyl formamide is added during 10 min. The reaction mixture is heated under stirring and nitrogen at 100° for 3 hours. Is is worked up as described under example 6 and the residue is recrystallised from a mixture of methylene chloride and hexane to afford 1-N, N-dimethyl-carbamoyl-2-oxo-3-[1-methyl-5-nitro-imidazolyl-(2)]-tetrahydroimidazole which melts at 190°–191°.

The starting material required is prepared as follows:

A mixture of 86 g of ethylene urea and 118 g of N,N-dimethyl carbamoyl-chloride in 200 ml ethylene dichloride is heated under reflux for 3 hrs. under nitrogen. The solution is evaporated off to dryness and the residue dissolved in chloroform and chromatographed on a column of 1.5 kg of silica gel. The fractions that eluted with 5% methanol in chloroform are combined and recrystallized from a mixture of methylene chloride and hexane to afford 1-N,N-dimethyl-carbamoyl-2-oxo-tetrahydroimidazole which melts at 134°–136°.

EXAMPLE 10

To a suspension of 4.5g of 50% sodium hydride in 10 ml dry dimethyl formamide is added under stirring during 15 min., a solution of 16g of 1-ethyl-sulphonyl-2-oxo-tetrahydroimidazole in 30 ml dry dimethyl formamide. The reaction is stirred under nitrogen at 50° for 45 min. and a solution of 18.5 g of 1-methyl-2-methyl-sulphonyl-5-nitro-imidazole in 30 ml dry dimethyl formamide is added all at once and the reaction mixture heated at 100° for 3 hrs.

It is worked up in the manner described under example 6 and the residue is recrystallized from a mixture of methylene chloride and hexane to afford 1-N-ethyl-sulphonyl-2-oxo-3-[1-methyl-5-nitro-imidazolyl-(2)]-tetrahydroimidazole which melts at 176°–177°.

The starting material required is prepared as follows:

A mixture of 29.2g of ethyleneurea and 43.7 g of ethane sulphonyl chloride is heated at 110° for 3 hrs under nitrogen. The reaction mixture is triturated with 30 ml methanol and filtered. The filtrate is evaporated off and the residue is dissolved in chloroform and chromatographed on a column of 750 g of silica gel. The fraction which eluted with 5% methanol in chloroform, is recrystallized from a mixture of methylene chloride and hexane to afford 1-ethylsulphonyl-2-oxo-tetrahydroimidazole which melts at 114°–116°.

EXAMPLE 11

To a suspension of 1.2 g of 50% sodium hydride in 10 ml dry dimethyl formamide is added under stirring during 15 minutes, a solution of 5.8 of 1-(4-fluoro-phenylsulphonyl)-2-oxo-tetrahydroimidazole in 28 ml dry dimethyl formamide. The reaction mixture is stirred under nitrogen at room temperature for 1 hr and then at 50° for for an other hour. A solution of 5 g of 1-methyl-2-methylsulphonyl-3-nitroimidazole in 10 ml dry dimethyl formamide is added all at once. The reaction mixture is heated under stirring and nitrogen at 100° for 3 hrs. and worked up in the manner described under example 6. The residue is chromatographed on a column of 150 g silica gel. The fractions which eluted with 2.5% methanol in chloroform gives a crystalline substance which is recrystallised from a mixture of methylene chloride and hexane to afford 1-N-(4-fluorophenylsulphonyl)-2-oxo-3-[1-methyl-5-nitroimidazolyl-(2)]-tetrahydroimidazole which melts at 198°–200°.

The starting material required is prepared as follows:

A mixture of 17.2 g of ethyleneurea and 19.5 g of p-fluorobenzene sulphonyl chloride is heated at 110° for 3 ½ hrs. The residue is recrystallized from a mixture of methanol and water to afford 1-(4-fluorophenylsulphonyl)-2-oxo-tetrahydroimidazole which melts at 183°–185°.

EXAMPLE 12

A solution of 0.4 g of 2-oxo-3-[1-methyl-4-nitroimidazolyl-(2)]-tetrahydroimidazole in 8 ml dry dimethyl formamide is added dropwise to a suspension of 0.1 g of 50% sodium hydride in 2 ml dry dimethyl formamide. The reaction mixture is stirred at room temperature for 15 minutes and a solution of 0.2 g of methyl isocyanate in 2 ml dry dimethyl formamide is added and the reaction mixture heated for 3 hrs. at 100° and worked up in the manner described under example 6. The residue is chromatographed on a column of 40 g silica gel. The fraction which eluted with 5% methanol in chloroform affords 1-N-methyl-carbamoyl-2-oxo-3-[1-methyl-5-nitro-imidazolyl-(2)]-tetrahydroimidazole which melts at 176°–177°.

EXAMPLE 13

To a stirred suspension of 1.3 g of 50% sodium hydride dispersion in mineral oil in 20 ml dry dimethyl formamide is added dropwise a solution of 1-piperidinocarbonyl-2-oxo-tetrahydroimidazole in 15 ml dimethylformamide at ambient temperature. The temperature of the reaction is raised to 50° and stirred for 30 min. A solution of 5.12 g of 1-methyl-2-methyl-sulfonyl-5-nitro-imidazole in 20 ml dimethyl formamide is added dropwise in the course of 20 min, the temperature raised to 95° and maintained for 1 hr. The solvent is removed under reduced pressure, the residue washed with ether and treated with water containing crushed ice. The residue after removal of the aqueous layer is treated with isopropanol ether (5:1). The colourless granular precipitate is recrystallised from ethyl acetate-hexane to afford 1-piperidino-2-oxo-3-[1-methyl-5-nitro-imidazolyl-(2)]-tetrahydroimidazole melting at 152°.

EXAMPLE 14

To a stirred suspension of 1.92 g of 50% sodium hydride dispersion in mineral oil in 25 ml dry dimethyl formamide is added dropwise a solution of 7.96 g of 1-morpholinocarbonyl-2-oxo-tetrahydroimidazole in 15 ml dry dimethylformamide at ambient temperature. The above suspension is stirred at 50° for 30 min. A solution of 8.2 g of 1-methyl-2-methyl sulfonyl-5-nitroimidazole in 15 ml dimethyl formamide is added in the course of 5 min. The temperature of the reaction is raised to 95° and stirring continued for 2 hrs. The solvent is removed under reduced pressure, the residue is washed with ether and treated with crushed ice. The solid obtained is filtered to give 1-morpholinocarbonyl-2-oxo-3-[1-methyl-5-nitro-imidazolyl-(2)]-tetrahydroimidazole melting at 180° after crystallization from ether.

1-Morpholinocarbonyl-2-oxo-tetrahydroimidazole used as starting material is prepared as follows: To a stirred solution of 22.27 g of 1-chloro-carbonyl-2-oxo-tetrahydro imidazole in 80 ml anhydrous benzene is added dropwise a solution of 26.1 g of morpholine in 20 ml benzene. The mixture is refluxed for 4 hrs. The product is filtered off, treated with a saturated solution of NaHCO$_3$ and filtered. Recrystallization from isopropanol affords 1-morpholinocarbonyl-2-oxo-tetrahydroimidazole melting at 158°.

EXAMPLE 15

A solution of 2.9 g 1-(methylsulphonyl)-2-oxo-3-[1-methyl-5-nitroimidazolyl (2)]-tetrahydroimidazole and 1.9 g ethyloxonium fluoborate in 200 ml dry chloroform is set aside at room temperature for 72 hrs. A thick oil separates out, which crystallizes on treatment with alcohol. The solid is filtered off, boiled with acetone and filtered. The residue is crystallized from aqueous alcohol to give 1-methyl-2-[3-(methylsulphonyl)-2-oxo-tetrahydroimidazolyl (1)] - 3-ethyl-5-nitroimidazolium fluoborate of the formula

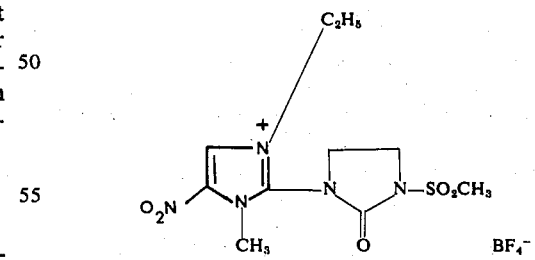

melting at 265°–267°.

EXAMPLE 16

A solution of 3.0 g 1-(methylsulphonyl)-2-oxo-3-[1-methyl-5nitroimidazolyl (2)]-tetrahydroimidazole in 30 ml dimethylformamide containing 3.0 g potassiumiodide is heated under reflux for 16 hours. The solvent is removed in vacuo and the residue treated with water and filtered. The filtrate is made acidic with 2N hydrochloric acid, cooled and filtered to remove unreacted starting material. The filtrate is cooled further and the crystals that separate are filtered off and recrystallized twice from acetone-methanol to give 1-(methylsulphonyl-2-oxo-3-[1-methyl-4-nitroimidazolyl(2)]-tetrahydroimidazole melting at 180°–181°.

EXAMPLE 17

A solution of 3.0g 1-(methylthiocarbamoyl)-2-oxo-3-[1-methyl-5-nitroimidazolyl (2)]-tetrahydroimidazole in 25 ml dimethylformamide containing 3.0 g potassium iodide is heated under reflux for 16 hr. The solvent is removed in vacuo and water added to the residue. The mixture is filtered and the precipitate washed sucessively with hot ethanol and methanol and crystallized twice from acetone-methanol to give 1-(methylthiocarbamoyl)-2-oxo-3-[1-methyl-4-nitroimidazolyl (2)]-tetrahydroimidazole melting at 239°–241°.

EXAMPLE 18

A solution of 0.49 g 1-(methylsulphonyl)-2-oxo-tetrahydroimidazole in 5 ml dimethylformamide is stirred with 0.15 g of a 50% suspension of sodium hydride in mineral oil at 50° for 1 hr. It is then treated with 0.57 g of 1-methyl-2-(methylsulfinyl)-5-nitroimidazole and the solution heated and stirred at 100° for 3 hours. The solvent is evaporated off in vacuo and the water added to the residue. The crystalline precipitate is filtered off and recrystallized from acetone-methanol to give 1-(methylsulphonyl)-2-oxo-3-[1-methyl-5-nitroimidazolyl(2)]-tetrahydroimidazole melting at 202°–204° and is identical with the preparation described in Example 4.

The starting 1-methyl-2-(methylsulfinyl)-5-nitroimidazole for the above reaction is made as follows:

A solution of 3.4 g 1-methyl-2-(methylmercapto)-5-nitroimidazole and 5 ml 30% aqueous hydrogen peroxide in 20 ml methoxyethanol is heated at 100° with freshly prepared titanium dioxide for 6 hrs. It is then diluted with water and filtered. The filtrate is extracted with chloroform and the chloroform layer evaporated to give 2.5 g of an oil which solidifies slowly upon standing. The solid is crystallized once from ethanol and then from chloroform-ether to give 1-methyl-2-(methylsulfinyl)-5-nitroimidazole.

EXAMPLE 19

To a suspension of 6.1 g 50% sodium hydride in 20 ml dry dimethyl formamide is added under stirring during 15 min. a solution of 30 g 1-(N,N-diethylsulphamoyl)-2-oxo-tetrahydroimidazole in 50 ml dry dimethyl formamide. The reaction mixture is stirred under nitrogen at 50° for 1 hour and a solution of 25.6 g of 1-methyl-2-methylsulphonyl-5-nitro-imidazole in 40 ml of dry dimethyl formamide is added all at once. The reaction is heated under stirring and nitrogen at 95° for 3 hours. The solvent is removed by distillation in vacuo and the residue triturated with 100 ml water. The resulting suspension is extracted with ethylene dichloride, dried and evaporated to dryness. The residue is chromatographed on a column of silica gel and the fraction that elutes with 1% methanol in chloroform affords a crystalline mass. This is recrystallized from a mixture of methylene chloride and ether to afford 1-N,N-diethyl sulphamoyl-2-oxo-3-[1-methyl-5-nitroimidazolyl-(2)]tetrahydroimidazole which melts at 146°–147°.

The starting material required for the above reaction is prepared as follows:

A mixture of 5.16 g of ethylene urea and 90 g of N,N-diethyl-sulphamoyl-chloride is heated at 110° for 3 hours. The reaction mixture is cooled and triturated with 300 ml of methanol, filtered and the filtrate evaporated off to dryness and the residue dissolved in 5% methanol in chloroform and chromatographed on a column of silica gel. That fraction which elutes with 5% methanol in chloroform is recrystallized from a mixture of methylenechlorid and hexane to give 1-(N,N-diethylsulphamoyl)--2-oxo-tetrahydroimidazole which melts at 80°–82°.

EXAMPLE 20

To a stirred suspension of 1.6 g of 50% sodium hydride dispersion in mineral oil in 30 ml dry dimethyl formamide is added during 15 min. a solution of 5.9 g of 1-pyrrolidino-carbonyl-2-oxo-tetrahydroimidazole in 15 ml dry dimethyl formamide. The reaction is stirred under nitrogen at 50° for 1 hour and a solution of 6.6 g of 1-methyl-2-methyl-sulphonyl-5-nitroimidazole in 20 ml dry dimethyl formamide is added all at once. The mixture is heated under stirring and nitrogen at 95° for 1 hour. The solvent is removed by distillation in vacuo and the residue is triturated with water and extracted with ethylene dichloride, dried and evaporated to dryness. The residue is chromatographed over silica gel and that fraction which elutes with 3% methanol in chloroform affords a crystalline mass. This is recrystallised from a mixture of methylene chloride and hexane to afford 1-pyrrolidino-carbonyl-2-oxo-3-[1-methyl-5-nitro-imidazolyl(2)]-tetrahydroimidazole which melts at 155°–156°.

The starting material required for the above reaction is prepared as follows:

A mixture of 40 g ethylene urea and 72 g of 1-pyrrolidino-carbonyl chloride (b.p. 100°–104°/4.5 mm Hg.) is heated at 110° for 3 hours. The reaction mixture is cooled, 200 ml of chloroform added, the insoluble material filtered off and the filtrate evaporated to dryness. It is chromatographed on a column of silica gel. That fraction which elutes with 4% of methanol in chloroform is recrystallised from ethylacetate to give 1-pyrrolidino-carbonyl-2-oxo-tetrahydroimidazole which melts at 153°–154°.

EXAMPLE 21

To a suspension of 3.5 g of 50% sodium hydride in 20 ml dimethyl formamide is added under stirring during 15 minutes, a solution of 15.6 g of 1-pyrrolidino-sulphonyl-2-oxo-tetrahydroimidazole in 40 ml dry dimethyl formamide. The reaction mixture is stirred under nitrogen at 50° for 1 hour, and a solution of 14.4 g of 1-methyl-2-methyl-sulphonyl-5-nitroimidazole in 30 ml dry dimethyl formamide is added all at once. The reaction mixture is heated under stirring and nitrogen at 95° for 3 hours. The solvent is removed by distillation in vacuo and the residue is triturated with 50 ml of water when a crystalline precipitate is formed. This is filtered and recrystallised from a mixture of methylene chloride and ether to afford 1-pyrrolidino-sulphonyl-2-oxo-3-[1-methyl-5-nitro-imidazolyl-(2)]-tetrahydroimidazole which melts at 226°.

The starting material required for the above reaction is prepared as follows:

A mixture of 30 g of ethyleneurea and 64.5 g of pyrrolidino-1-sulphonylchloride (b.p. 120°/11 mm Hg.) is heated at 110° for 3 hours. The reaction mixture is cooled, dissolved in 300 ml chloroform, filtered, the filtrate evaporated off and the residue is redissolved in 2.5% methanol in chloroform and chromatographed on a column of silicagel. That fraction which elutes with 2.5% methanol in chloroform affords 1-pyrrolidino-sulphonyl-2-oxo-tetrahydroimidazole which is recrystallized from ethylacetate, m.p. 150°.

EXAMPLE 22

To a stirred suspension of 1.92 g of 50% sodium hydride dispersion in mineral oil in 20 ml dry dimethyl formamide is added dropwise a solution of 9.3 g of 1-piperidino-sulfonyl-2-oxo-tetrahydroimidazole in 15 ml dimethyl formamide at ambient temperature. The temperature of the reaction is raised to 50° and stirred for 30 min. A solution of 8.2 g of 1-methyl-2-methylsulfonyl-5-nitroimidazole in 25 ml of dimethyl formamide is added in one lot and the temperature of the reaction is maintained for 2 hrs. at 100°. The solvent is removed under reduced pressure and the residue treated with water containing crushed ice. The residue after removal of the aqueous layer is treated with isopropanol-ether (5:1). The pale yellow precipitate so obtained is recrystallised from ethyl acetate to afford 1-piperidino-sulfonyl-2-oxo-3-[1-methyl-5-nitroimidazolyl-(2)]-tetrahydroimidazole melting at 192°.

The starting material is prepared as follows:

To 17.4 of ethyleneurea is added with shaking 36 g of piperidinosulfonyl chloride (b.p. 130°/11m) and the mixture kept under nitrogen at 100° for 3 hrs. The mixture is cooled and the gummy material treated with methanol-isopropanol (1:1) to give a granular product of 1-piperidinosulfonyl-2-oxo-tetrahydroimidazole which melts at 201° on recrystallization from methanol.

EXAMPLE 23

To a solution of 8 g of 1-(methylsulphonyl)-2-oxo-4-methyl-2,3,4,5-tetrahydroimidazole in 30 ml of dry dimethyl formamide is added 2.2 g of a 50% slurry of sodium hydride in mineral oil. The mixture is stirred at room temperature for 1 hour. A solution of 9.2 g of 1-methyl-2-methanesulphonyl-5-nitroimidazole in 20 ml of dry dimethylformamide is now added and the mixture is stirred at room temperature for 3 hours. The solvent is then removed in vacuo and the residue dissolved in water, upon cooling, a crystalline precipitate is obtained, which is filtered off and recrystallized from a mixture of methylene chloride and ether to afford 1-(methylsulphony)-2-oxo-3-[1-methyl-5-nitroimidazolyl-(2)]-4-methyl-tetrahydroimidazole, melting at 199°–200°.

The starting 1-(methylsulphonyl)-2-oxo-4-methyl-2,3,4,5-tetrahydroimidazole for the above reaction is prepared as follows:

A mixture of 10 g of 4-methyl-2-imidazolidinone and 11.5 g of methane sulphonyl chloride is heated for 3 hours at 120° with stirring, while a stream of nitrogen is bubbled in to remove hydrogen chloride. After cooling, water is added and the mixture heated on a steambath till a crystalline powder is formed. This is filtered and chromatographed on a column of silicagel using chloroform as solvent. The fraction which eluted with a mixture of chloroform-methanol (97:3) afforded the titled compound which crystallizes from a mixture of methylene chloride and hexane and melts at 129°–130°.

What is claimed is:

1. Compounds of the formula I

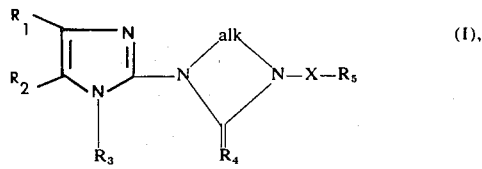

wherein one of the groups $R_1$ and $R_2$ is a hydrogen or lower alkyl and the other a nitro group, $R_3$ is a lower alkyl, hydroxy-lower alkyl, lower-alkoxy-lower-alkyl, lower-alkylsulphonyl-lower-alkyl or amino-lower-alkyl, $R_4$ is an oxo or thioxo group, X is a carbonyl or thiocarbonyl group and $R_5$ when X is a carbonyl group is a lower alkoxy, amino, loweralkylamino, or diloweralkylamino group, and when X is a thiocarbonyl group $R_5$ is a lower alkyl, aryl, amino, alkylamino or diloweralkylamino group and alk is 1,2-ethylene, their N-oxides and pharmaceutically acceptable salts.

2. Compounds of formula I according to claim 1, wherein $R_1$, $R_3$, $R_5$ and X have the meanings as defined in claim 1, $R_2$ is a nitro group, $R_4$ is an oxo group, their salts and N-oxides.

3. Compounds of formula I according to claim 1, wherein $R_2$, $R_3$, $R_5$ and X have the meanings as defined in claim 1, $R_1$, is a nitro group, $R_4$ is an oxo group and alk represents a lower alkylene residue of 2–4 carbon atoms, their salts and N-oxides.

4. Compounds of formula I according to claim 1, wherein $R_1$ and $R_3$ have the meanings as defined in claim 1, $R_2$ is a nitro group, X is a carbonyl group, $R_4$ is an oxo group, and $R_5$ represents a lower alkoxy, amino, lower alkylamino or dialkylamino group, their salts and N-oxides.

5. Compounds of formula I according to claim 1, wherein $R_2$ and $R_3$ have the meanings as defined in claim 1, $R_1$ is a nitro group, X is a carbonyl group and $R_4$ is an oxo group, and $R_5$ represents a lower alkoxy, amino, lower alkylamino or dialkylamino group, their salts and N-oxides.

6. Compounds of formula I according to claim 1, wherein $R_1$ and $R_3$ have the meanings as defined in claim 1, $R_2$ is a nitro group, X is a thiocarbonyl group, $R_4$ is an oxo group and $R_5$ represents a lower alkyl, lower alkoxy, aryl, amino, lower alkylamino or diloweralkylamino group, their salts and N-oxides.

7. Compounds of formula I according to claim 1, wherein $R_2$ and $R_3$ have the meanings as defined in claim 1, $R_1$ is a nitro group, X is a thiocarbonyl group and $R_4$ is an oxo group and $R_5$ represents a lower alkyl, lower alkoxy, aryl, amino, lower alkylamino or diloweralkylamino group, their salts and N-oxides.

8. 1-(Methylthiocarbamoyl)-2-oxo-3-[1-methyl-5-nitroimidazolyl-(2)]-tetrahydroimidazole or a pharmaceutically acceptable salt thereof.

9. 1-(Benzylthiocarbamoyl)-2-oxo-3-[1-methyl-5-nitroimidazolyl-(2)]-tetrahydroimidazole or a pharmaceutically acceptable salt thereof.

10. 1-(Methylcarbamoyl)-2-oxo-3-[1-methyl-5-nitroimidazolyl-(2)]-tetrahydroimidazole or a pharmaceutically acceptable salt thereof.

11. 1-N,N-Diethylcarbamoyl-2-oxo-3-[1-methyl-5-nitroimidazolyl-(2)]-tetrahydroimidazole or a pharmaceutically acceptable salt thereof.

12. 1-N,N-Dimethylcarbamoyl-2-oxo-3-[1-methyl-5-nitroimidazolyl-(2)]-tetrahydroimidazole or a pharmaceutically acceptable salt thereof.

13. 1-(N-Ethylthiocarbamoyl)-2-oxo-3-[1-methyl-5-nitroimidazolyl-(2)]-tetrahydroimidazole, or a pharmaceutically acceptable salt thereof.

14. A compound of the formula I

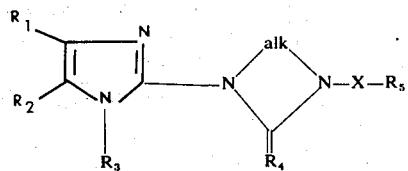

wherein one of the groups $R_1$ and $R_2$ is a hydrogen or lower alkyl and the other a nitro group, $R_3$ is lower alkyl, hydroxy-lower alkyl, lower-alkoxy-lower alkyl, lower-alkylsulphonyl-lower-alkyl or amino-lower-alkyl, $R_4$ is an oxo group, X is a carbonyl or thiocarbonyl group and $R_5$ when X is a carbonyl group is amino, lower-alkylamino, or diloweralkylamino group, and when X is a thiocarbonyl, $R_5$ is an amino, alkylamino or diloweralkylamino group and alk is 1,2-ethylene, a pharmaceutically acceptable salt thereof and N-oxides.

15. A therapeutic composition comprising an antibacterially effective amount of compound of formula I as defined in claim 1 and a pharmaceutically acceptable solid carrier or diluent therefore.

16. An antibacterial active composition useful as gram negative active agent comprising an anti-bacterially effective amount of a compound having the general formula I as defined in claim 1 or a pharmaceutically acceptable acid addition salt of such a compound and a pharmaceutically acceptable diluent or carrier therefore.

17. An antiprotozoic active composition useful as antiprotozoic active agent against trichomonads and amoeba comprising an antiprotozoically effective amount of a compound having the general formula I as defined in claim 1 or a pharmaceutically acceptable acid addition salt of such a compound and a pharmaceutically acceptable diluent or carrier therefore.

18. An anthelmenthic active composition useful as anthelminthic active agent against schistosoma comprising an anthelmenthically effective amount of a compound having the general formula I as defined in claim 1 or a pharmaceutically acceptable acid addition salt of such a compound and a pharmaceutically acceptable diluent or carrier therefore.

* * * * *